(12) United States Patent
Hodges et al.

(10) Patent No.: US 10,632,238 B1
(45) Date of Patent: Apr. 28, 2020

(54) BREASTFEEDING DEVICE

(71) Applicants: Christian Hodges, Columbus, OH (US); Bethany Hodges, Columbus, OH (US)

(72) Inventors: Christian Hodges, Columbus, OH (US); Bethany Hodges, Columbus, OH (US)

( * ) Notice: Subject to any disclaimer, the term of this patent is extended or adjusted under 35 U.S.C. 154(b) by 205 days.

(21) Appl. No.: 15/889,287

(22) Filed: Feb. 6, 2018

(51) Int. Cl.
*A61M 1/06* (2006.01)
*A61J 17/00* (2006.01)

(52) U.S. Cl.
CPC ............ *A61M 1/068* (2014.02); *A61J 17/008* (2015.05); *A61M 1/064* (2014.02); *A61M 2205/3337* (2013.01); *A61M 2209/088* (2013.01)

(58) Field of Classification Search
CPC ........ A61M 1/06; A61M 1/066; A61M 1/062; A61M 1/068; A61M 2209/088; A61M 1/064; A61J 13/00; A61J 15/0011
See application file for complete search history.

(56) References Cited

U.S. PATENT DOCUMENTS

| | | | |
|---|---|---|---|
| 949,414 A | 2/1910 | Cunningham | |
| D382,687 S | 8/1997 | Schaffner | |
| 6,379,327 B2 | 4/2002 | Lundy | |
| 6,440,100 B1 | 8/2002 | Prentiss | |
| D576,283 S | 9/2008 | Marshall | |
| 7,607,965 B1 | 10/2009 | Frazier | |
| 9,107,991 B1 * | 8/2015 | Frere | A61M 1/06 |
| 2008/0262420 A1 * | 10/2008 | Dao | A61M 1/06 604/74 |
| 2011/0270164 A1 | 11/2011 | Bane | |
| 2015/0038945 A1 * | 2/2015 | McCabe | A61M 1/068 604/514 |

FOREIGN PATENT DOCUMENTS

WO   2009134274 A   11/2009

* cited by examiner

*Primary Examiner* — Rebecca E Eisenberg
(74) *Attorney, Agent, or Firm* — Kyle A. Fletcher, Esq.

(57) ABSTRACT

The breastfeeding device comprises a suction assembly that attaches to one of the mother's breasts, a pump assembly that provides suction to express milk from the mother's breast and collect it in a reservoir, a pacifier that allow a baby to feed on collected breast milk, and interconnecting flexible tubing. In some embodiments, the breastfeeding device may also comprise a breastfeeding garment which may allow the mother to use the suction assembly while wearing clothing and which may help to hold the suction assembly in place. A shutoff valve on the outlet of the pump assembly may allow the pacifier and associated tubing to be disconnected without loss of breast milk when the baby is not feeding.

15 Claims, 5 Drawing Sheets

_US 10,632,238 B1_

BREASTFEEDING DEVICE

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of breastfeeding, more specifically, a device, which allows a nursing mother to discreetly collect breast milk and feed her baby.

SUMMARY OF INVENTION

The breastfeeding device comprises a suction assembly that attaches to one of the mother's breasts, a pump assembly that provides suction to express milk from the mother's breast and allow a baby to feed on collected breast milk. In some embodiments, the breastfeeding device may also comprise a breastfeeding garment which may allow the mother to use the suction assembly while wearing clothing and which may help to hold the suction assembly in place. A shutoff valve on the outlet of the pump assembly may allow the pacifier and associated tubing to be disconnected without loss of breast milk when the baby is not feeding.

An object of the invention is to allow a nursing mother to discreetly pump breast milk to a pacifier.

Another object of the invention is to allow a baby to consume collected breast milk from the pacifier.

A further object of the invention is to allow the mother to disconnect the tubing and pacifier that the baby uses to feed without loss of breast milk when the tubing and pacifier are not needed.

Yet another object of the invention is to provide a breastfeeding garment that allows use of the breastfeeding device in public.

These together with additional objects, features and advantages of the breastfeeding device will be readily apparent to those of ordinary skill in the art upon reading the following detailed description of the presently preferred, but nonetheless illustrative, embodiments when taken in conjunction with the accompanying drawings.

In this respect, before explaining the current embodiments of the breastfeeding device in detail, it is to be understood that the breastfeeding device is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the breastfeeding device.

It is therefore important that the claims be regarded as including such equivalent construction insofar as they do not depart from the spirit and scope of the breastfeeding device.

It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description. As used herein, the word "or" is intended to be inclusive.

Figure 1:
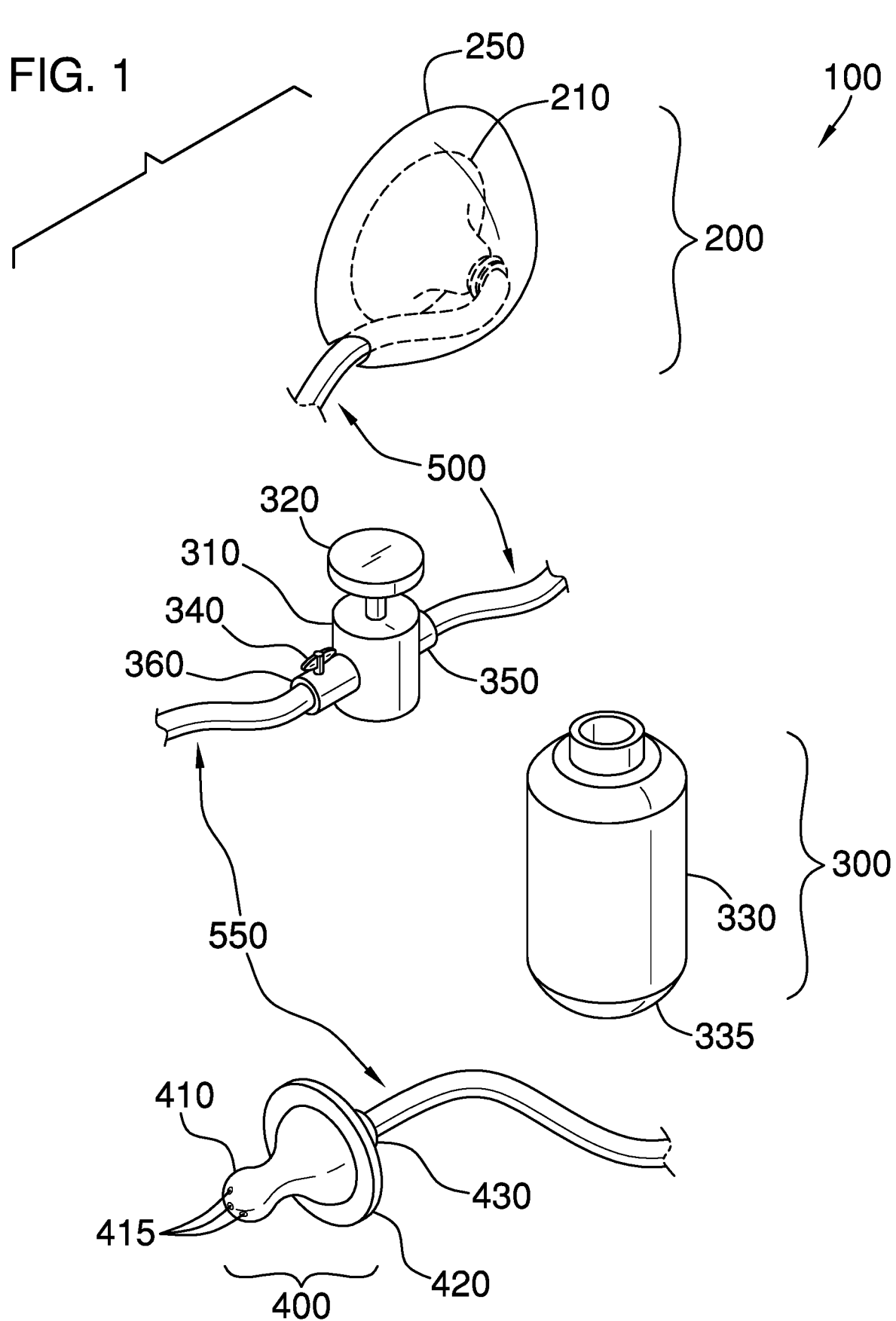
FIG. 1 is a perspective view of an embodiment of the disclosure.
Figure 2:
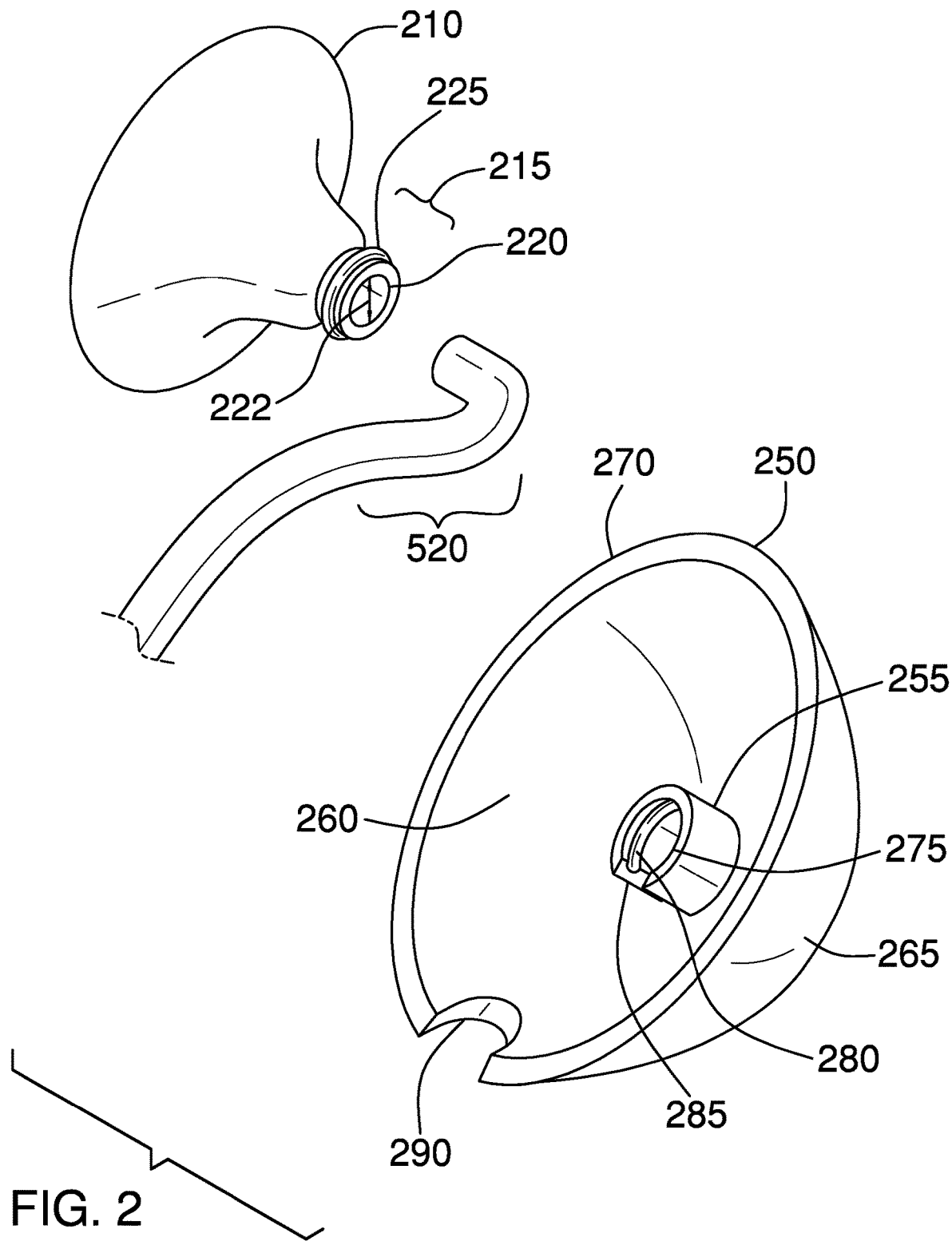
FIG. 2 is a detail view of an embodiment of the disclosure showing elements of the suction assembly.
Figure 3:
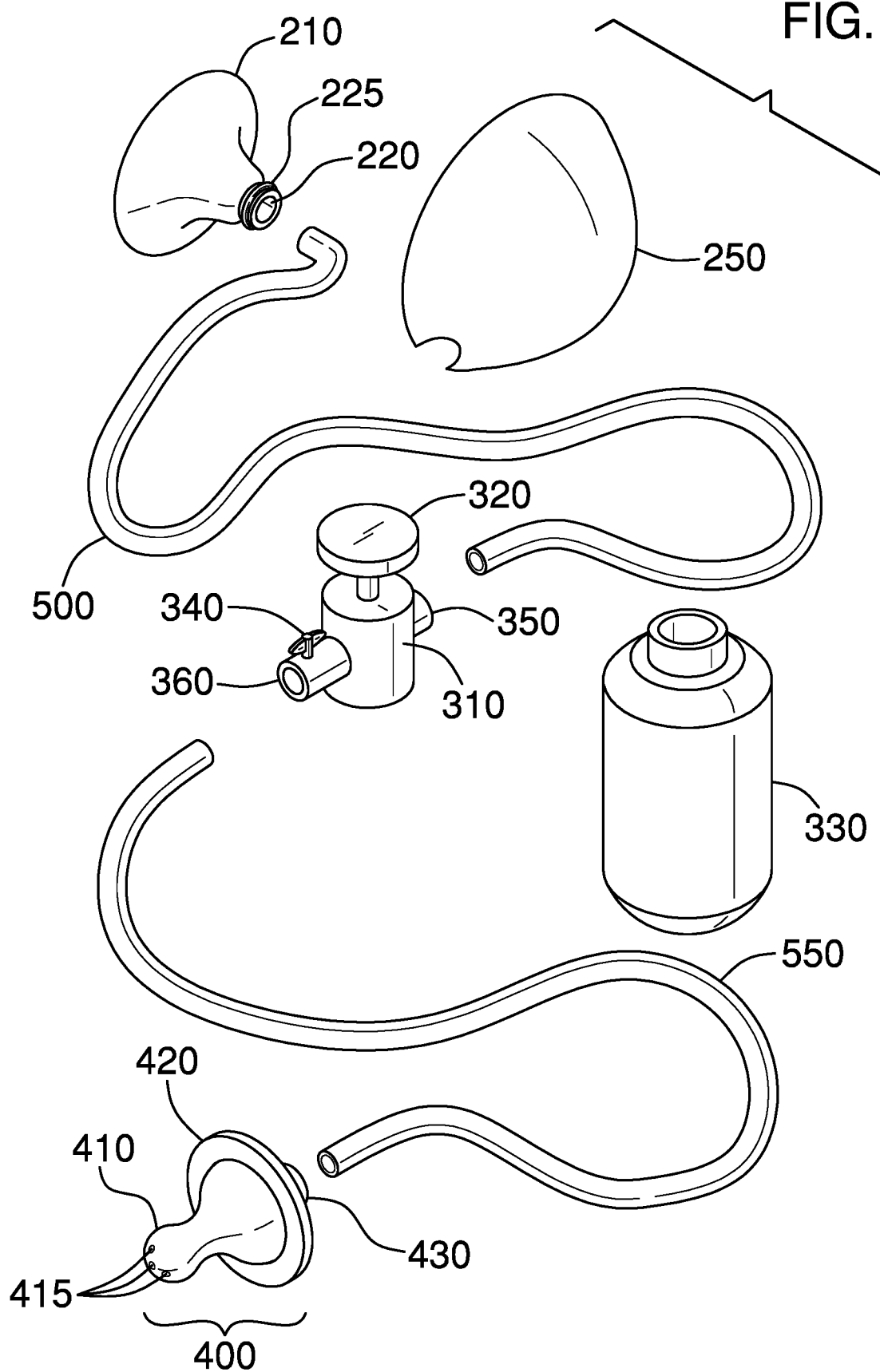
FIG. 3 is an exploded view of an embodiment of the disclosure.
Figure 4:
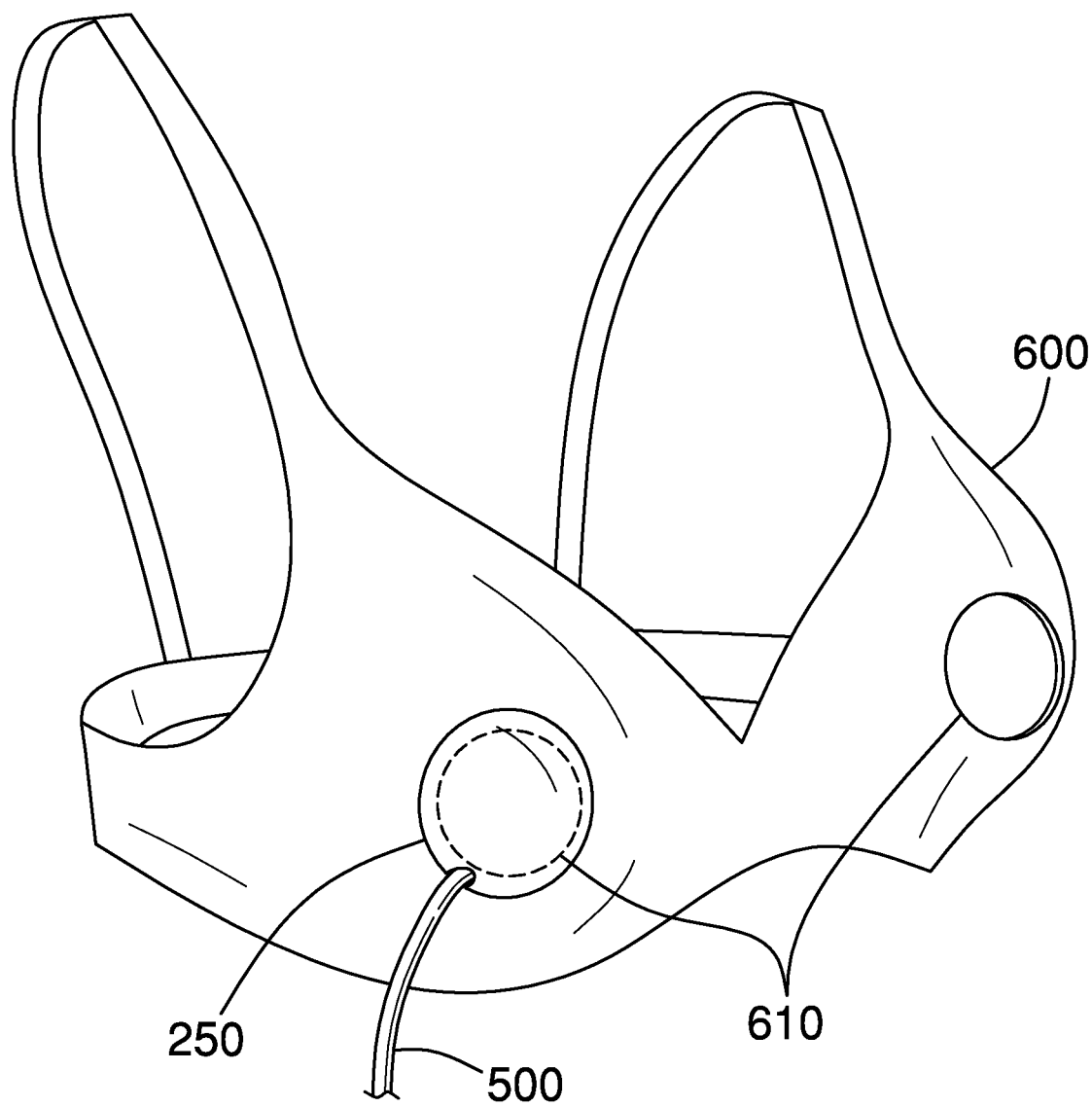
FIG. 4 is a detail view of an embodiment of the disclosure showing the breastfeeding garment.
Figure 5:
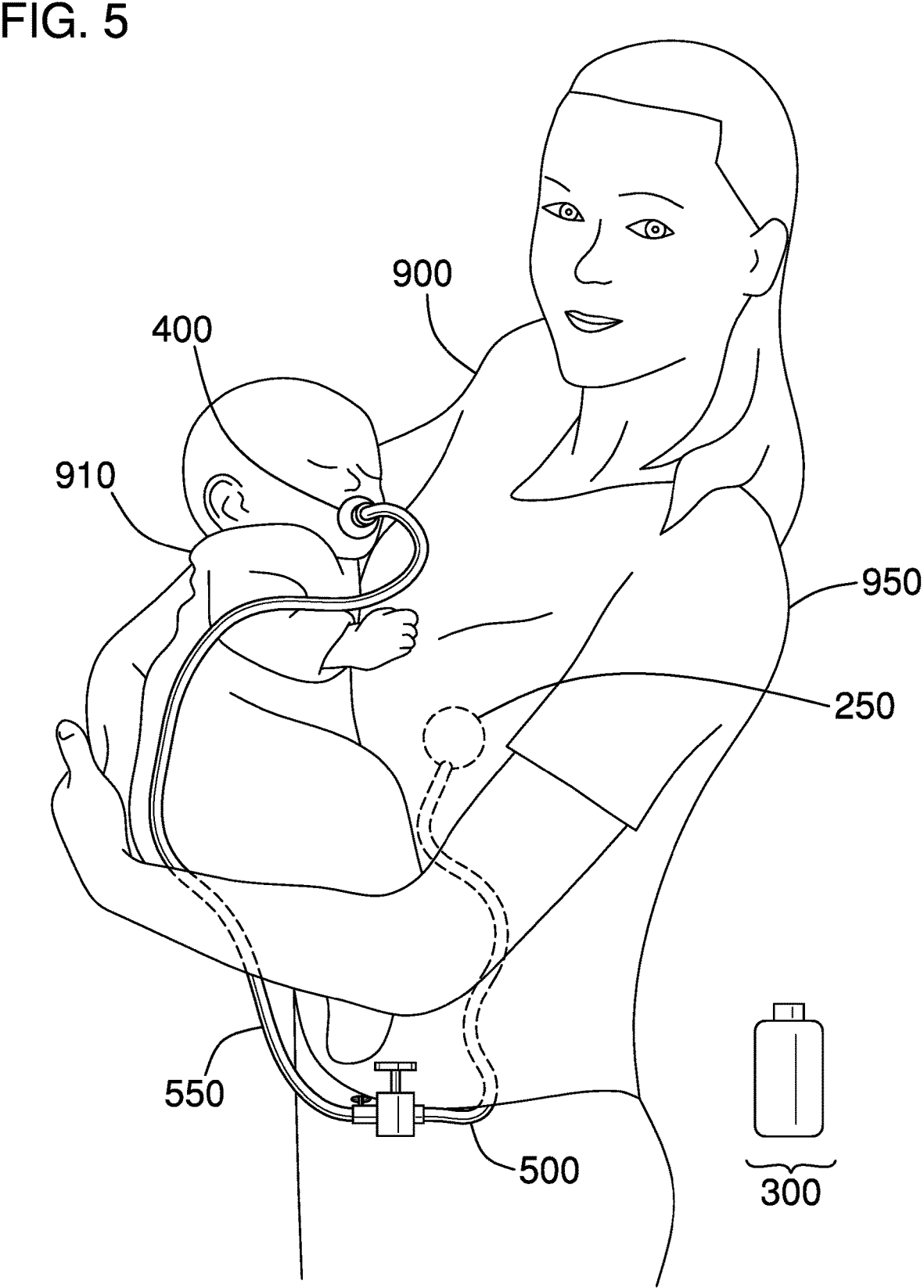
FIG. 5 is a view of an embodiment of the disclosure while in use.

Detailed reference will now be made to a first potential embodiment of the disclosure, which is illustrated in FIGS. 1 through 5.

The breastfeeding device 100 (hereinafter invention) comprises a suction assembly 200, a pump assembly 300, a pacifier 400, an upper tubing 500 and a lower tubing 550. The breastfeeding device 100 may allow a mother 900 to discreetly breastfeed a baby 910 in public. Using the breastfeeding device 100, the mother 900 may pump breast milk 920 from a breast 930 using the pump assembly 300 and the suction assembly 200 attached to the breast 930. Any of the breast milk 920 that remains in the upper tubing 500 may be evacuated and collected in a reservoir 330. The reservoir 330 is detachable with respect to the pump assembly 300.

The suction assembly 200 comprises a cup 210 and a cover 250. The cup 210 is a cone-shaped element, which covers a mother's nipple. The cup 210 is held against the breast 930 by suction generated by the pump assembly 300; the suction may be conveyed to the cup 210 by the upper tubing 500. A narrow end 215 of the cup 210 terminates with a hose opening 220 where the upper tubing 500 may be attached. An inside diameter of the hose opening 222 matches the dimension of an outside diameter of the upper tubing. The narrow end 215 of the cup 210 comprises a retention ridge 225 around the outside of the narrow end 215. The retention ridge 225 is used to hold the cover 250 in place.

The cover 250 is a dome-shaped element that may protect the cup 210 and the upper tubing 500. The cover 250 may improve the appearance of the mother 900 by providing a more natural contour for clothing of the mother 900, making it less obvious that the breastfeeding device 100 is in use. The cover 250 comprises a cup receptacle 255 at the center of a convex side of the cover 265. The cup receptacle 255 is tubular and projects directly towards the breast 930.

The cup receptacle 255 comprises a cup opening 275, a snap groove 280, and a first tubing notch 285. The cup opening 275 is an open end of the cup receptacle 255 into which the narrow end 215 of the cup 210 slides. The diameter of the cup opening 275 matches the diameter of the narrow end 215 of the cup 210, excluding the retention ridge 225. The snap groove 280 is a groove around inside of the cup receptacle 255. The diameter of the snap groove 280 is larger than the diameter of the cup opening 275. The diameter of the snap groove 280 matches the diameter of the retention ridge 225. When the cover 250 is pressed onto the cup 210, the narrow end 215 of the cup 210 slides into the cup opening 275 of the cup receptacle 255 and the snap groove 280 interlocks with the retention ridge 225 on the cup 210 to hold the cover 250 in place. The first tubing notch 285 allows the upper tubing 500 to pass from the narrow end 215 of the cup 210 and out from under the cup receptacle 255 without interfering with the fit of the cover 250 on the cup 210.

An outer rim of the cover 270 rests upon the breast 930. The cover 250 comprises a second tubing notch 290 at the outer rim of the cover 270. The second tubing notch 290 is at least as large as the outside diameter of the upper tubing to allow the upper tubing 500 to pass from a concave side of the cover 260 to the convex side of the cover 265. This allows the upper tubing 500 to exit from the cup 210 and the cover 250 and reach to the pump assembly 300.

The pump assembly 300 comprises a pump 310, a pump handle 320, the reservoir 330, a suction line 335, a shutoff valve 340, an intake connection 350 and an output connection 360. The pump assembly 300 may create suction that starts the flow of the breast milk 920 from the mother's nipple, through the cup 210, through the upper tubing 500, and into the pump 310. The breast milk 920 flowing into the pump 310 is directed into the lower tubing 550. To create suction, the mother 900 moves the pump handle 320 up and down repeatedly.

If the shutoff valve 340 is in an open position, the breast milk 920 may be sucked via the suction line 335. The breast milk 920 is sucked through the lower tubing 550 to the pacifier 400. When the shutoff valve 340 is in a closed position, the upper tubing 500 and the pacifier 400 may be disconnected from the breastfeeding device 100 without loss of the breast milk 920. The upper tubing 500 connects to the reservoir 330 via the intake connection 350. The lower tubing 550 connects to the reservoir 330 via the output connection 360.

The pacifier 400 comprises a nipple 410, a guard 420 and a pacifier hose connection 430. The pacifier 400 is made from a soft, pliable material. In a preferred embodiment, the pacifier 400 is made from silicone. The pacifier 400 may be sucked on via the baby 910 even when not feeding. The lower tubing 550 connects to the pacifier 400 via the pacifier hose connection 430. The breast milk 920 flowing into the pacifier 400 from the lower tubing 550 continues to flow through the pacifier 400 until it reaches the nipple 410 of the pacifier 400. One or more holes 415 in the nipple 410 allow the baby 910 to suck the breast milk 920 out of the pacifier 400. The guard 420 prevents the baby 910 from swallowing the pacifier 400.

The upper tubing 500 is a flexible tube. One end of the upper tubing 500 connects to the hose opening 220 of the cup 210 and the other end of the upper tubing 500 connects to the intake connection 350 of the pump 310. The upper tubing 500 transfers the breast milk 920 from the cup 210 to the pump 310. In some embodiments, one end of the upper tubing 500 may be pre-formed into a hook shape 520 to facilitate connection to the cup 210 and to facilitate placement of the upper tubing 500 under the cover 250. The hook shape 520 is a bend of 90 degrees or more starting within 20 mm of the end of the upper tubing 500 that attaches to the cup 210. The hook shape 520 allows the upper tubing 500 to change direction immediately upon exiting the cup 210 and to follow the contour of the cup 210 so that the upper tubing 500 stays against the breast 930.

The lower tubing 550 is a flexible tube. One end of the lower tubing 550 connects to the output connection 360 of the pump 310 and the other end of the lower tubing 550 connects to the pacifier hose connection 430 of the pacifier 400. An outside diameter of the lower tubing matches an inside diameter of the pacifier hose connection. The lower tubing 550 transfers the breast milk 920 from the reservoir 330 to the pacifier 400.

In some embodiments, the breastfeeding device 100 further comprises a breastfeeding garment 600. The breastfeeding garment 600 fits snugly over both of the breasts 930 of the mother 900 and provides two access holes 610 directly over both of the mother's nipples. An outer garment 950 may be worn over the breastfeeding garment 600. Use of the breastfeeding garment 600 allows the cup 210, the upper tubing 500, and the cover 250 to be used while still being fully dressed. In some embodiments, the breastfeeding garment 600 may partially cover the cup 210 to help hold the cup 210 in place. In some embodiments, the breastfeeding garment 600 may be a bra with the two access holes 610.

With respect to the above description, it is to be realized that the optimum dimensional relationship for the various components of the invention described above and in FIGS. 1 through 5, include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

What is claimed is:

1. A breastfeeding device comprising:
a suction assembly, a pump assembly, a pacifier, an upper tubing and a lower tubing;
wherein the breastfeeding device is adapted to allow the mother to pump breast milk from a breast using the pump assembly and the suction assembly attached to the breast;

wherein unused the breast milk is drained from the upper tubing, and collected within a reservoir;

wherein the reservoir is detachably coupled with the pump assembly;

wherein the breastfeeding device is adapted to allow the baby to consume the breast milk by sucking it through the pacifier;

wherein the suction assembly comprises a cup and a cover;

wherein the cup is a cone-shaped element which is adapted to cover a mother's nipple;

wherein the cup is adapted to be held against the breast by suction generated by the pump assembly;

wherein the suction is conveyed to the cup by the upper tubing;

wherein a narrow end of the cup terminates with a hose opening;

wherein the upper tubing attaches to the hose opening;

wherein an inside diameter of the hose opening matches the dimension of an outside diameter of the upper tubing;

wherein the narrow end of the cup comprises a retention ridge around the outside of the narrow end;

wherein the retention ridge is used to hold the cover in place.

2. The breastfeeding device according to claim 1 wherein the cover is a dome-shaped element that protects the cup and the upper tubing;

wherein the cover is adapted to provide a more natural contour for clothing of the mother, making it less obvious that the breastfeeding device is in use;

wherein the cover comprises a cup receptacle at the center of a convex side of the cover;

wherein the cup receptacle is tubular and projects directly towards the breast.

3. The breastfeeding device according to claim 2 wherein the cup receptacle comprises a cup opening, a snap groove, and a first tubing notch;

wherein the cup opening is an open end of the cup receptacle into which the narrow end of the cup slides;

wherein the diameter of the cup opening matches the diameter of the narrow end of the cup, excluding the retention ridge;

wherein the snap groove is a groove around inside of the cup receptacle;

wherein the diameter of the snap groove is larger than the diameter of the cup opening;

wherein the diameter of the snap groove matches the diameter of the retention ridge;

wherein when the cover is pressed onto the cup, the narrow end of the cup slides into the cup opening of the cup receptacle and the snap groove interlocks with the retention ridge on the cup to hold the cover in place;

wherein the first tubing notch allows the upper tubing to pass from the narrow end of the cup and out from under the cup receptacle without interfering with the fit of the cover on the cup.

4. The breastfeeding device according to claim 3 wherein an outer rim of the cover is adapted to rest upon the breast;

wherein the cover comprises a second tubing notch at the outer rim of the cover;

wherein the second tubing notch is at least as large as the outside diameter of the upper tubing to allow the upper tubing to pass from a concave side of the cover to the convex side of the cover.

5. The breastfeeding device according to claim 4 wherein the pump assembly comprises a pump, a pump handle, the reservoir, a suction line, a shutoff valve, an intake connection and an output connection;

wherein the pump assembly creates suction that starts the flow of the breast milk from the mother's nipple, through the cup, through the upper tubing, and into the pump;

wherein to create suction, the pump handle is moved up and down repeatedly.

6. The breastfeeding device according to claim 5 wherein if the shutoff valve is in an open position, the breast milk is sucked out via the suction line;

wherein the breast milk flows through the lower tubing to the pacifier;

wherein when the shutoff valve is in a closed position, the upper tubing and the pacifier can be disconnected from the breastfeeding device without loss of the breast milk;

wherein the upper tubing connects to the reservoir via the intake connection;

wherein the lower tubing connects to the reservoir via the output connection.

7. The breastfeeding device according to claim 6 wherein the pacifier comprises a nipple, a guard and a pacifier hose connection;

wherein the pacifier is made from a pliable material;

wherein the pacifier is adapted to be sucked on by the baby even when not feeding;

wherein the pacifier is adapted to deliver the breast milk to the baby.

8. The breastfeeding device according to claim 7 wherein the pacifier is made from silicone.

9. The breastfeeding device according to claim 6 wherein the lower tubing connects to the pacifier via the pacifier hose connection;

wherein the breast milk is configured to flow into the pacifier from the lower tubing, and continues to flow through the pacifier until it reaches the nipple of the pacifier;

wherein one or more holes in the nipple are adapted to allow the baby to suck the breast milk out of the pacifier;

wherein the guard prevents the baby from swallowing the pacifier.

10. The breastfeeding device according to claim 9 wherein the upper tubing is a flexible tube;

wherein one end of the upper tubing connects to the hose opening of the cup;

wherein the other end of the upper tubing connects to the intake connection of the pump;

wherein the upper tubing transfers the breast milk from the cup to the pump.

11. The breastfeeding device according to claim 10 wherein one end of the upper tubing is pre-formed into a hook shape to facilitate connection to the cup and to facilitate placement of the upper tubing under the cover;

wherein the hook shape is a bend of 90 degrees or more starting within 20 mm of the end of the upper tubing that attaches to the cup;

wherein the hook shape allows the upper tubing to change direction immediately upon exiting the cup and to follow the contour of the cup so that the upper tubing stays against the breast.

12. The breastfeeding device according to claim 10 wherein the lower tubing is a flexible tube;

wherein one end of the lower tubing connects to the output connection of the pump;

wherein the other end of the lower tubing connects to the pacifier hose connection of the pacifier;

wherein the lower tubing transfers the breast milk to the pacifier.

13. The breastfeeding device according to claim 12 wherein the breastfeeding device further comprises a breastfeeding garment;

wherein the breastfeeding garment is adapted to form fit over both of the breasts of the mother;

wherein the breastfeeding garment provides two access holes directly over both of the mother's nipples.

14. The breastfeeding device according to claim 13 wherein the breastfeeding garment partially covers the cup to help hold the cup in place.

15. The breastfeeding device according to claim 13 wherein the breastfeeding garment is a bra with the two access holes.

* * * * *